(12) United States Patent
Benson et al.

(10) Patent No.: US 10,048,228 B2
(45) Date of Patent: Aug. 14, 2018

(54) SYSTEMS AND METHODS FOR ESTIMATING FUEL TYPE AND FUEL PROPERTIES USING SONIC SPEED

(71) Applicant: CUMMINS INC., Columbus, IN (US)

(72) Inventors: Donald J. Benson, Columbus, IN (US); David M. Carey, Greenwood, IN (US)

(73) Assignee: CUMMINS INC., Columbus, IN (US)

( * ) Notice: Subject to any disclaimer, the term of this patent is extended or adjusted under 35 U.S.C. 154(b) by 0 days.

(21) Appl. No.: 15/288,930

(22) Filed: Oct. 7, 2016

(65) Prior Publication Data

US 2017/0102363 A1   Apr. 13, 2017

Related U.S. Application Data (60) Provisional application No. 62/238,655, filed on Oct. 7, 2015.

(51) Int. Cl.
*G01N 29/036* (2006.01)
*G01N 33/22* (2006.01)

(52) U.S. Cl.
CPC .......... *G01N 29/036* (2013.01); *G01N 33/22* (2013.01); *G01N 2291/022* (2013.01)

(58) Field of Classification Search
None
See application file for complete search history.

(56) References Cited

U.S. PATENT DOCUMENTS

| | | | | |
|---|---|---|---|---|
| 2,405,100 A | * | 7/1946 | Stephens | F17D 1/20 137/565.18 |
| 2,437,446 A | * | 3/1948 | Stephens | F16L 55/04 138/26 |
| 2,474,555 A | * | 6/1949 | Stephens | F16L 55/04 417/441 |
| 2,518,832 A | * | 8/1950 | Stephens | G01L 19/0007 138/26 |
| 2,795,374 A | * | 6/1957 | Isakoff | F04B 39/0055 138/26 |
| 3,706,227 A | * | 12/1972 | Gottron | F15C 1/005 137/842 |
| 4,003,242 A | * | 1/1977 | Houben | G01N 29/024 137/804 |

(Continued)

FOREIGN PATENT DOCUMENTS

EP   1 253 410   10/2002

OTHER PUBLICATIONS

International Search Report and Written Opinion dated Dec. 16, 2016 in corresponding International Application No. PCT/US2016/056107.

*Primary Examiner* — Shelley Chen
(74) *Attorney, Agent, or Firm* — Faegre Baker Daniels LLP (57) ABSTRACT

Diagnostic systems including a pressure sensor, a determiner in communication with the pressure sensor, wherein the determiner is structured to estimate a sonic speed of a fuel based on identification of a fundamental oscillation frequency are disclosed. Also disclosed are diagnostic methods comprising receiving, by a pressure interpreter, a pressure signal, determining, by a determiner in communication with the pressure interpreter, a fundamental frequency of oscillation of the pressure signal, and determining, by the determiner, a sonic speed of a fuel based on the fundamental frequency of oscillation.

20 Claims, 7 Drawing Sheets

(56) References Cited

U.S. PATENT DOCUMENTS

| | | | | |
|---|---|---|---|---|
| 4,164,867 | A * | 8/1979 | Hickling | F02P 5/152 374/117 |
| 6,088,418 | A * | 7/2000 | Martin | G21C 9/004 261/124 |
| 6,250,137 | B1 | 6/2001 | Takahashi et al. | |
| 6,823,834 | B2 | 11/2004 | Benson et al. | |
| 6,975,402 | B2 * | 12/2005 | Bisson | G01N 21/1702 356/432 |
| 7,000,450 | B2 | 2/2006 | Unger et al. | |
| 7,171,847 | B2 | 2/2007 | Kuhn | |
| 7,392,491 | B2 | 6/2008 | Ismailov | |
| 7,523,640 | B2 | 4/2009 | DiFoggio et al. | |
| 7,775,092 | B2 | 8/2010 | Murphy et al. | |
| 7,921,691 | B2 | 4/2011 | Di-Foggio et al. | |
| 7,930,930 | B2 | 4/2011 | Ungaro et al. | |
| 2004/0095579 | A1 * | 5/2004 | Bisson | G01N 21/1702 356/432 |
| 2006/0096388 | A1 * | 5/2006 | Gysling | G01F 1/666 73/861.03 |
| 2006/0236976 | A1 | 10/2006 | Carlson | |
| 2007/0204679 | A1 | 9/2007 | Fitch et al. | |
| 2009/0178474 | A1 * | 7/2009 | Bailey | F02D 19/0628 73/114.38 |
| 2013/0276758 | A1 | 10/2013 | Pursifull | |
| 2014/0002640 | A1 * | 1/2014 | Kurokawa | G01F 1/661 348/135 |
| 2016/0370327 | A1 * | 12/2016 | Moldover | G01M 3/24 |
| 2017/0321621 | A1 * | 11/2017 | Zimmer | F02D 41/40 |

* cited by examiner

SYSTEMS AND METHODS FOR ESTIMATING FUEL TYPE AND FUEL PROPERTIES USING SONIC SPEED

CROSS-REFERENCE TO RELATED APPLICATIONS

This application claims priority to U.S. Provisional Application Ser. No. 62/238,655 entitled SYSTEMS AND METHODS FOR ESTIMATING FUEL TYPE AND FUEL PROPERTIES USING SONIC SPEED, filed on Oct. 7, 2015, the entire disclosure of which is hereby expressly incorporated by reference.

FIELD OF THE DISCLOSURE

This disclosure relates to systems and methods for estimating the fuel type and fuel properties. More specifically, this disclosure relates to systems and methods for estimating the fuel type and fuel properties using the sonic speed.

BACKGROUND

Fuel for internal combustion engines can vary for many reasons, such as seasonal blends and source (e.g., biodiesel). Compliance with various environmental regulations, improved fuel efficiency, improved engine performance, and the ability to adapt engine performance to various mixtures of fuels has been of increasing concern.

Some current fueling monitoring, diagnostics, and/or controls can incorporate closed-loop fueling algorithms. The mass of fuel removed from a pressurized volume may be calculated from the following equation:

$$m = \frac{\rho V}{\beta} \Delta P \quad \text{Equation 1}$$

where $\rho$ is the fuel density, V is the pressurized volume, $\beta$ is the bulk modulus of fuel in the pressurized volume, and $\Delta P$ is the pressure drop.

Using the bulk modulus equation:

$$c = \sqrt{\frac{\beta}{\rho}} \quad \text{Equation 2}$$

where c is the speed of sound, $\rho$ is the fuel density, and $\beta$ is the bulk modulus of fuel in the pressurized volume, we may be able to determine the mass removed from a pressurized volume in terms of the speed of sound, volume, and change in pressure, as illustrated by Equation 3 below:

$$m = \frac{V}{c^2} \Delta P \quad \text{Equation 3}$$

Because the sonic speed of a fluid may be dependent on fuel temperature, pressure, and fluid composition, the various conventional methods do not adequately monitor the mass of fuel removed from a pressurized volume, and they require a variety of various sensors monitoring pressure and temperature, which increases the cost, complexity, and maintenance of various engine components.

Moreover, many of these conventional methods and systems do not account for the fuel characteristics, such as blends, classifications, or temperature. Accordingly, when fuel tanks contain a variety of fuels (e.g., mixtures of biofuel and fossil fuels) or operate at varying temperatures, engine diagnostics, control, and performance can suffer.

A need therefore exists to address issues of more accurately determining the mass of fuel removed from pressurized volumes and determination of various characteristics of the fuel.

SUMMARY

In some embodiments, diagnostic systems may include a pressure sensor, a determiner in communication with the pressure sensor, wherein the determiner is structured to estimate a sonic speed of a fuel based on identification of a fundamental oscillation frequency.

In various embodiments, engines may include a pressure sensor, a determiner in communication with the pressure sensor, wherein the determiner is structured to estimate a sonic speed of a fuel in response to identification of a fundamental oscillation frequency.

Diagnostic methods may comprise receiving, by a pressure interpreter, a pressure signal, determining, by a determiner in communication with the pressure interpreter, a fundamental frequency of oscillation of the pressure signal, and determining, by the determiner, a sonic speed of a fuel in response to determining the fundamental frequency of oscillation.

BRIEF DESCRIPTION OF THE DRAWINGS

The above mentioned and other features and objects of this disclosure, and the manner of attaining them, will become more apparent and the disclosure itself will be better understood by reference to the following description of an embodiment of the disclosure taken in conjunction with the accompanying drawings, wherein.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplification set out herein illustrates an embodiment of the disclosure, in one form, and such exemplifications are not to be construed as limiting the scope of the disclosure in any manner.

DETAILED DESCRIPTION

The embodiments disclosed below are not intended to be exhaustive or limit the disclosure to the precise form disclosed in the following detailed description. Rather, the embodiments are chosen and described so that others skilled in the art may utilize its teachings.

One of ordinary skill in the art will realize that the embodiments provided can be implemented in hardware, software, firmware, and/or a combination thereof. Programming code according to the embodiments can be implemented in any viable programming language such as C, C++, HTML, XTML, JAVA or any other viable high-level programming language, or a combination of a high-level programming language and a lower level programming language.

Diagnostic systems disclosed herein may include a pressure sensor, a determiner in communication with the pressure sensor, wherein the determiner is structured to estimate a sonic speed of a fuel based on identification of a fundamental oscillation frequency.

As used herein, the term "frequency" is not intended to mean only one and only one frequency. Thus, in various embodiments and/or configurations, multiple fundamental oscillation frequencies from which reinforcing or unique information about the system and/or fuel may be obtained.

Accordingly, diagnostic systems disclosed herein may include a pressure sensor, a determiner in communication with the pressure sensor, wherein the determiner is structured to estimate a sonic speed of a fuel based on identification of a fundamental oscillation frequency or frequencies.

As described above, fueling monitoring, diagnostics, and/or controls can incorporate closed-loop fueling algorithms. The mass of fuel removed from a pressurized volume may be calculated from the following equation:

$$m = \frac{\rho V}{\beta}\Delta P \qquad \text{Equation 1}$$

where $\rho$ is the fuel density, V is the pressurized volume, $\beta$ is the bulk modulus of fuel in the pressurized volume, and $\Delta P$ is the pressure drop.

Using the bulk modulus equation:

$$c = \sqrt{\frac{\beta}{\rho}} \qquad \text{Equation 2}$$

where c is the speed of sound, $\rho$ is the fuel density, and $\beta$ is the bulk modulus of fuel in the pressurized volume, we may be able to determine the mass removed from a pressurized volume in terms of the speed of sound, volume, and change in pressure, as illustrated by Equation 3 below:

$$m = \frac{V}{c^2}\Delta P \qquad \text{Equation 3}$$

Figure 7:
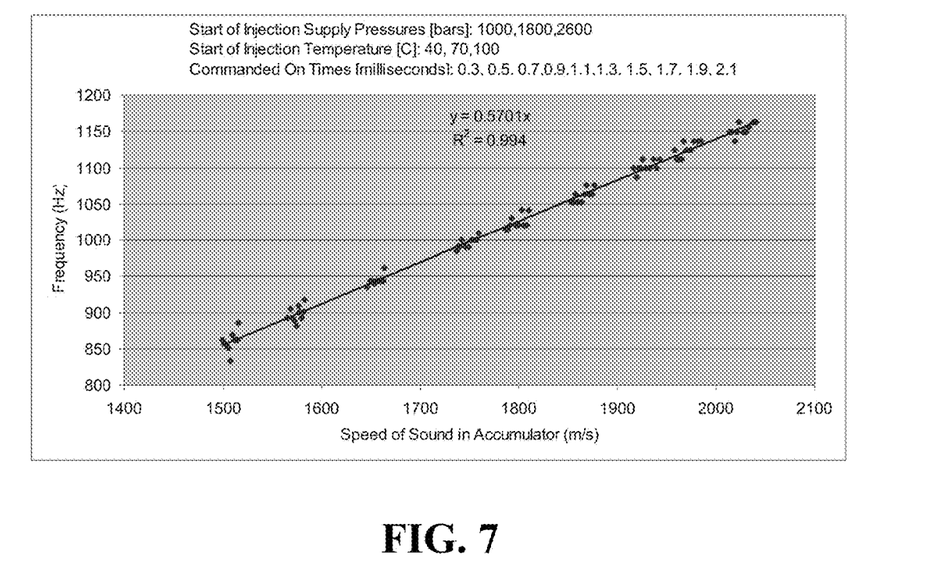
FIG. 7 contains data illustrating the relationship between sonic speed and frequency.

For example, with temporary reference to FIG. 7, an exemplary plot showing the relationship of the speed of sound in an accumulator to the natural frequency from experimental data is shown. As can be seen in the figure, there is a proportional relationship between the speed of sound in an accumulator and the natural frequency.

The diagnostic systems are not particularly limited and may be included as part of an engine, such as an internal combustion engine. The internal combustion engines may include a diesel engine, a gasoline engine, a flex fuel engine, hybrid engine, or other known internal combustion engines.

While the sonic speed of a fluid may be dependent on temperature, pressure, and fluid composition, sonic speed may be estimated using a natural frequency (i.e., a fundamental frequency of oscillation) from a pressure signal. As used herein, the term "fundamental frequency of oscillation" may include a measured, calculated, or estimated natural frequency from a signal, such as a pressure signal from an engine.

Figure 8:
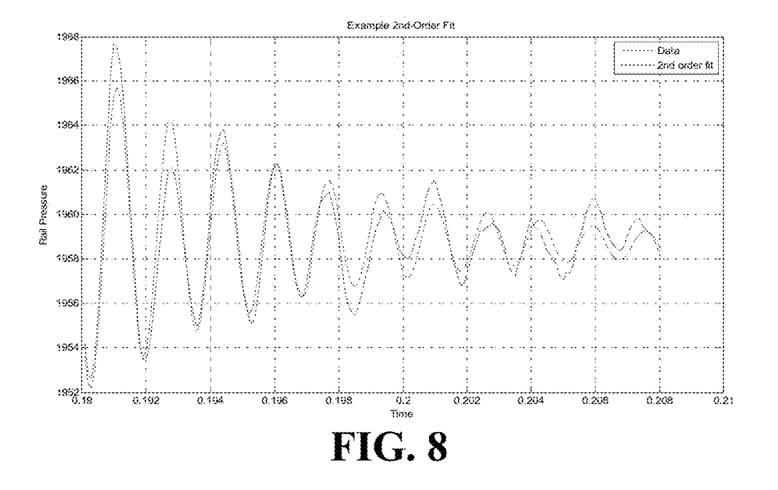
FIG. 8 illustrates exemplary pressure data.

The natural frequency may be calculated, determined, or estimated from measured pressure data, such as the pressure data shown in FIG. 8. Calculating, determining, or estimating the natural frequency can be accomplished by various different methods, such as using a Fourier transform, fitting a $2^{nd}$ order response, or a simple zero-crossing measurements. FIG. 8 illustrates the relationship between the measured data and a $2^{nd}$ order fit.

Thus, using the pressure measurements, the sonic speed may be determined from a fundamental frequency of oscillation. While the fundamental frequency may change with changes in pressure, temperature, and fuel type, using other relationships determinable from methods and systems disclosed herein, the sonic speed may be calculated from the fundamental frequency of oscillation.

One such relationship is by using a proportional relationship, such as that illustrated in Equation 4:

$$c = k \times f_n \qquad \text{Equation 4}$$

where k is the proportionality constant and $f_n$ is the fundamental frequency of oscillation.

The fundamental frequency of oscillation in a pressurized volume, such as a rail in an engine, may be measured during engine operation at several temperatures and operating conditions. The sonic speed may then be estimated as a function of temperature and pressure. For example, according to various embodiments, this estimation may be estimated with the following exemplary Equation 5:

$$c^2 = c_0 + c_1 P + c_2 T + c_3 P^2 + c_4 T^2 + c_5 PT \qquad \text{Equation 5}$$

where P is the pressure of the fuel, T is the temperature of the fuel, $c_0$, $c_1$, $c_2$, $c_3$, $c_4$, $c_5$, are regression coefficients.

In various embodiments, the number of samples of the fundamental frequency may be increased prior to calculating the sonic speed to account for noise, which may arise if there are numerous relatively short time intervals of pressure data, such as the period in between injections of fuel during operation of an engine. Accordingly, estimates of the fundamental frequency may occur over a time period, after a number of revolutions of the engine, or other criteria recognizable by those skilled in the art with the benefit of this disclosure.

Furthermore, the measurement of the true effective fuel temperature may be calculated from various models. Such models may incorporate or account for engine conditions, such as speed, rail pressure, and fueling to account for dynamic changes in temperature due to various dynamic operating conditions. For example, Equation 6 illustrates an exemplary equation according to various embodiments:

$$T = k_0 + k_1 T_{rail} + k_2 T_{coolant} + c_3 T_{inlet} + \dot{m}(k_4 P + k_5 T_{coolant} + k_6 T_{inlet}) \qquad \text{Equation 6}$$

where T is the modeled true effective temperature, $T_{coolant}$ is the measured coolant temperature, $T_{rail}$ is the measured rail temperature, $T_{inlet}$ is the pump inlet temperature, $\dot{m}$ is the mass flow rate (e.g., based on engine speed and fueling command), $k_0$, $k_1$, $k_2$, $k_3$, $k_4$, $k_5$, and $k_6$ are best-fit regression coefficients, and P is the rail pressure.

In various embodiments, the best-fit coefficients may be calculated off-line using measured engine data and/or they could be calculated on-line (e.g., during engine operation) by combining the sonic speed regression coefficients and driving the on-line regression for both sets of coefficients using the fundamental frequency of oscillation.

Accordingly, in various embodiments, the sonic speed may be used to calculate the fuel temperature and the mass of fuel removed from a pressurized system.

Figure 1:
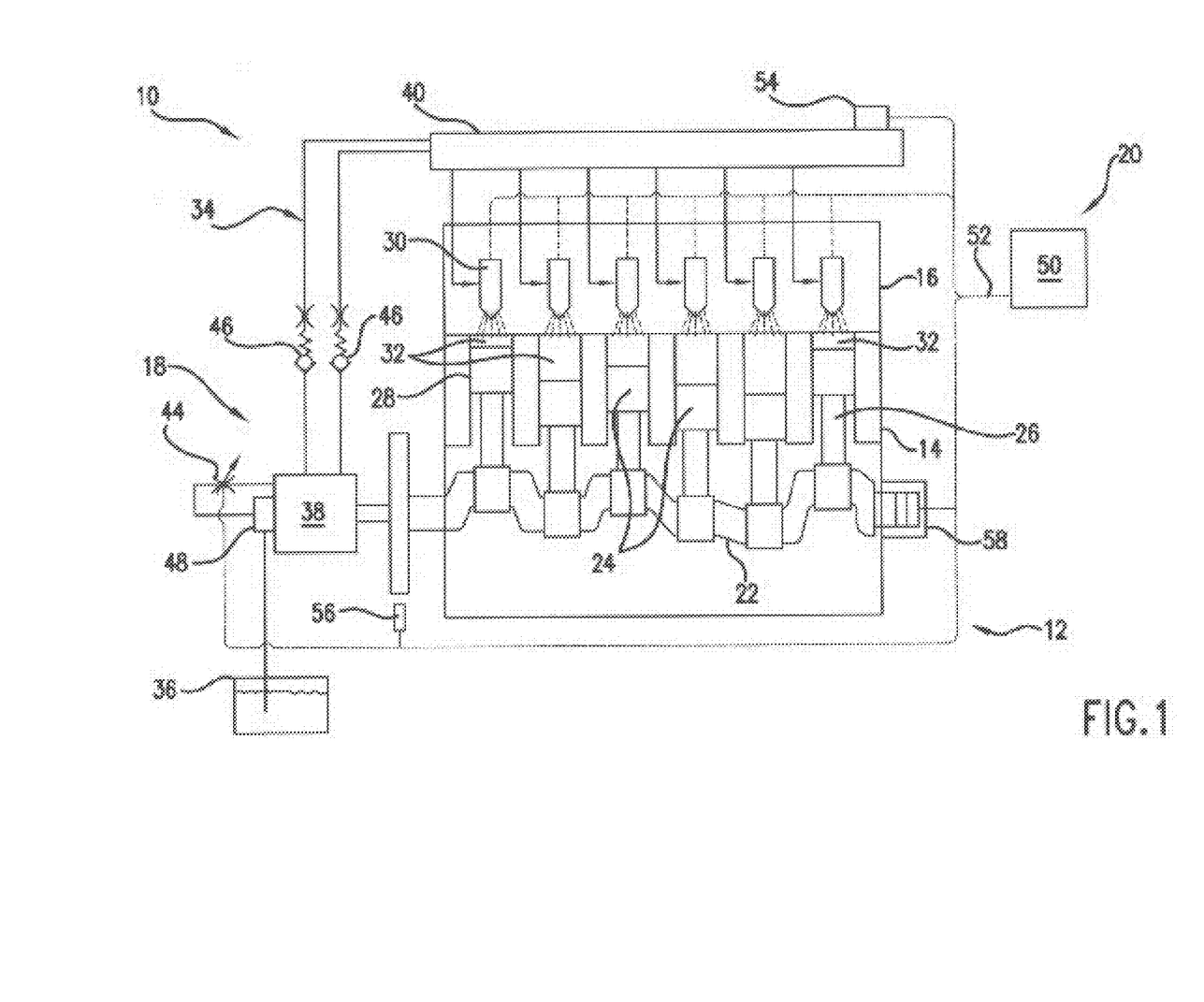
FIG. 1 illustrates a diagnostic system that forms part of an engine according to various embodiments.

Referring to FIG. 1, a portion of an internal combustion engine in accordance with a first exemplary embodiment of the present disclosure is shown as a simplified schematic and generally indicated at 10. Engine 10 includes a control system that generates a fuel injection signal that is transmitted to an electrical driver, where the fuel injection signal is amplified. The fuel injection signal is then transmitted to a fuel injector, which opens a nozzle or needle valve element to permit fuel to flow through the fuel injector into a combustion chamber. In order to calculate an actual on-time of the fuel injector, the control system uses diagnostic information available before the fuel injection signal is transmitted to the fuel injector to model and predict a pressure profile in a fuel system that provides high-pressure fuel to the fuel injector. The control system uses the pressure model along with a fueling command to calculate the fuel injector on-time. The information that may be used to model pressure in the fuel system may include a pump command, a fuel system set point or target fuel system pressure, pressure measurement signals from the fuel system, common fuel rail or accumulator dimensions, and fuel characteristics.

Engine 10 includes an engine body 12, which includes an engine block 14 and a cylinder head 16 attached to engine block 14, a fuel system 18, and a control system 20. Control system 20 receives signals from sensors located on engine 10 and transmits control signals to devices located on engine 10 to control the function of those devices. Engine body 12 includes a crank shaft 22, a plurality of pistons 24, and a plurality of connecting rods 26. Pistons 24 are positioned for reciprocal movement in a plurality of engine cylinders 28, with one piston 24 positioned in each engine cylinder 28. One connecting rod 26 connects each piston 24 to crank shaft 22. As will be seen, the movement of pistons 24 under the action of a combustion process in engine 10 causes connecting rods 26 to move crankshaft 22.

A plurality of fuel injectors 30 are positioned within cylinder head 16. Each fuel injector 30 is fluidly connected to a combustion chamber 32, each of which is formed by one piston 24, cylinder head 14, and the portion of engine cylinder 28 that extends between a respective piston 24 and cylinder head 14.

Fuel system 18 provides fuel to injectors 30, which is then injected into combustion chambers 32 by the action of fuel injectors 30, forming one or more injection events. Fuel system 18 includes a fuel circuit 34, a fuel tank 36, which contains a fuel, a high-pressure fuel pump 38 positioned along fuel circuit 34 downstream from fuel tank 36, and a fuel accumulator or rail 40 positioned along fuel circuit 34 downstream from high-pressure fuel pump 38. While fuel accumulator or rail 40 is shown as a single unit or element, accumulator 40 may be distributed over a plurality of elements that transmit or receive high-pressure fuel, such as fuel injector(s) 30, high-pressure fuel pump 38, and any lines, passages, tubes, hoses and the like that connect high-pressure fuel to the plurality of elements. Injectors 30 receive fuel from fuel accumulator 40. Fuel system 18 may further include an inlet metering valve 44 positioned along fuel circuit 34 upstream from high-pressure fuel pump 38 and one or more outlet check valves 46 positioned along fuel circuit 34 downstream from high-pressure fuel pump 38 to permit one-way fuel flow from high-pressure fuel pump 38 to fuel accumulator 40. Though not shown, additional elements may be positioned along fuel circuit 34. For example, inlet check valves may be positioned downstream from inlet metering valve 44 and upstream from high-pressure fuel pump 38, or inlet check valves may be incorporated in high-pressure fuel pump 38. Inlet metering valve 44 has the ability to vary or shut off fuel flow to high-pressure fuel pump 38, which thus shuts off fuel flow to fuel accumulator 40. Fuel circuit 34 connects fuel accumulator 40 to fuel injectors 30, which then provide controlled amounts of fuel to combustion chambers 32. Fuel system 18 may also include a low-pressure fuel pump 48 positioned along fuel circuit 34 between fuel tank 36 and high-pressure fuel pump 38. Low-pressure fuel pump 48 increases the fuel pressure to a first pressure level prior to fuel flowing into high-pressure fuel pump 38.

Control system 20 may include controller 50 and a wire harness 52. Many aspects of the disclosure are described in terms of sequences of actions to be performed by elements of a computer system or other hardware capable of executing programmed instructions, for example, a general purpose computer, special purpose computer, workstation, or other programmable data processing apparatus. It will be recognized that in each of the embodiments, the various actions could be performed by specialized circuits (e.g., discrete logic gates interconnected to perform a specialized function), by program instructions (software), such as logical blocks, program determiners being executed by one or more processors (e.g., one or more microprocessor, a central processing unit (CPU), and/or application specific integrated circuit), or by a combination of both. For example, embodiments can be implemented in hardware, software, firmware, middleware, microcode, or any combination thereof. The instructions can be program code or code segments that perform necessary tasks and can be stored in a machine-readable medium such as a storage medium or other storage(s). A code segment may represent a procedure, a function, a subprogram, a program, a routine, a subroutine, a determiner, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as programs, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or flash memory), or any other tangible medium capable of storing information.

In certain embodiments, the controller 50 includes one or more interpreters, determiners, or processors that functionally execute the operations of the controller. The description herein including interpreters, determiners, or processors emphasizes the structural independence of certain aspects of the controller 50, and illustrates one grouping of operations and responsibilities of the controller. Other groupings that execute similar overall operations are understood within the scope of the present application. Interpreters, determiners, and processors may be implemented in hardware and/or as computer instructions on a non-transient computer readable storage medium, and may be distributed across various hardware or computer based components.

Example and non-limiting implementation elements that functionally execute the operations of the controller include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Control system 20 may also include an accumulator pressure sensor 54 and a crank angle sensor. While pressure sensor 54 is described as being a pressure sensor, the term pressure sensor may be understood to include other devices that may be calibrated to provide a pressure signal that represents fuel pressure, such as a force transducer, strain gauge, or other device. Thus, according to various embodiments, a processor, such as a determiner, may be configured to receive a rail pressure signal from the pressure sensor.

According to various embodiments, the determiner may be configured to determine a mass of fuel removed from a pressurized volume, such as rail 40. Thus, in various embodiments, the pressurized volume is a fixed volume.

The crank angle sensor may be a toothed wheel sensor 56, a rotary Hall sensor 58, or other type of device capable of measuring the rotational angle of crankshaft 22. Control system 20 may use signals received from accumulator pressure sensor 54 and the crank angle sensor to determine the combustion chamber receiving fuel, which is then used to analyze the signals received from accumulator pressure sensor 54.

Controller 50 may be an electronic control unit that may monitor conditions of engine 10 or an associated vehicle in which engine 10 may be located. Controller 50 may be a single processor, a distributed processor, an electronic equivalent of a processor, or any combination of the aforementioned elements, as well as software, electronic storage, fixed lookup tables and the like. Controller 50 may include a digital or analog circuit. Controller 50 may connect to certain components of engine 10 by wire harness 52, though such connection may be by other means, including a wireless system. For example, controller 50 may connect to and provide control signals to inlet metering valve 44 and to fuel injectors 30.

When engine 10 is operating, combustion in combustion chambers 32 causes the movement of pistons 24. The movement of pistons 24 causes movement of connecting rods 26, which are drivingly connected to crankshaft 22, and movement of connecting rods 26 causes rotary movement of crankshaft 22. The angle of rotation of crankshaft 22 is measured by engine 10 to aid in timing of combustion events in engine 10 and for other purposes. The angle of rotation of crankshaft 22 may be measured in a plurality of locations, including a main crank pulley (not shown), an engine flywheel (not shown), an engine camshaft (not shown), or on the camshaft itself. Measurement of crankshaft 22 rotation angle may be made with toothed wheel sensor 56, rotary Hall sensor 58, and by other techniques. A signal representing the angle of rotation of crankshaft 22, also called the crank angle, is transmitted from toothed wheel sensor 56, rotary Hall sensor 58, or other device to control system 20.

Crankshaft 22 drives high-pressure fuel pump 38 and low-pressure fuel pump 48. The action of low-pressure fuel pump 48 pulls fuel from fuel tank 36 and moves the fuel along fuel circuit 34 toward inlet metering valve 44. From inlet metering valve 44, fuel flows downstream along fuel circuit 34 through inlet check valves (not shown) to high-pressure fuel pump 38. High-pressure fuel pump 38 moves the fuel downstream along fuel circuit 34 through outlet check valves 46 toward fuel accumulator or rail 40. Inlet metering valve 44 receives control signals from control system 20 and is operable to block fuel flow to high-pressure fuel pump 38. Inlet metering valve 44 may be a proportional valve or may be an on-off valve that is capable of being rapidly modulated between an open and a closed position to adjust the amount of fuel flowing through the valve.

Fuel pressure sensor 54 is connected with fuel accumulator 40 and is capable of detecting or measuring the fuel pressure in fuel accumulator 40. Fuel pressure sensor 54 sends signals indicative of the fuel pressure in fuel accumulator 40 to controller 50. Fuel accumulator 40 is connected to each fuel injector 30. Control system 20 provides control signals to fuel injectors 30 that determine operating parameters for each fuel injector 30, such as the length of time (on-time) fuel injectors 30 operate and the number of fueling pulses per a firing or injection event period, which determines the amount of fuel delivered by each fuel injector 30.

Certain operations described herein include operations to interpret and/or to determine one or more parameters or data structures. Interpreting or determining, as utilized herein, includes receiving values by any method known in the art, including at least receiving values from a datalink or network communication, receiving an electronic signal (e.g. a voltage, frequency, current, or PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

In various embodiments, the determiner may determine a characteristic of the fuel. Characteristics of fuel may include at least one of a temperature of the fuel, a classification of the fuel, or a composition of the fuel, or combinations thereof. From this classification or composition of the fuel from the determiner, many useful characteristics such as the heating value or density of the fuel can be estimated. Moreover, in some embodiments the characteristic may be stored by the determiner during operation of the engine, during shut-down, during start-up, or combinations thereof.

Figure 2:
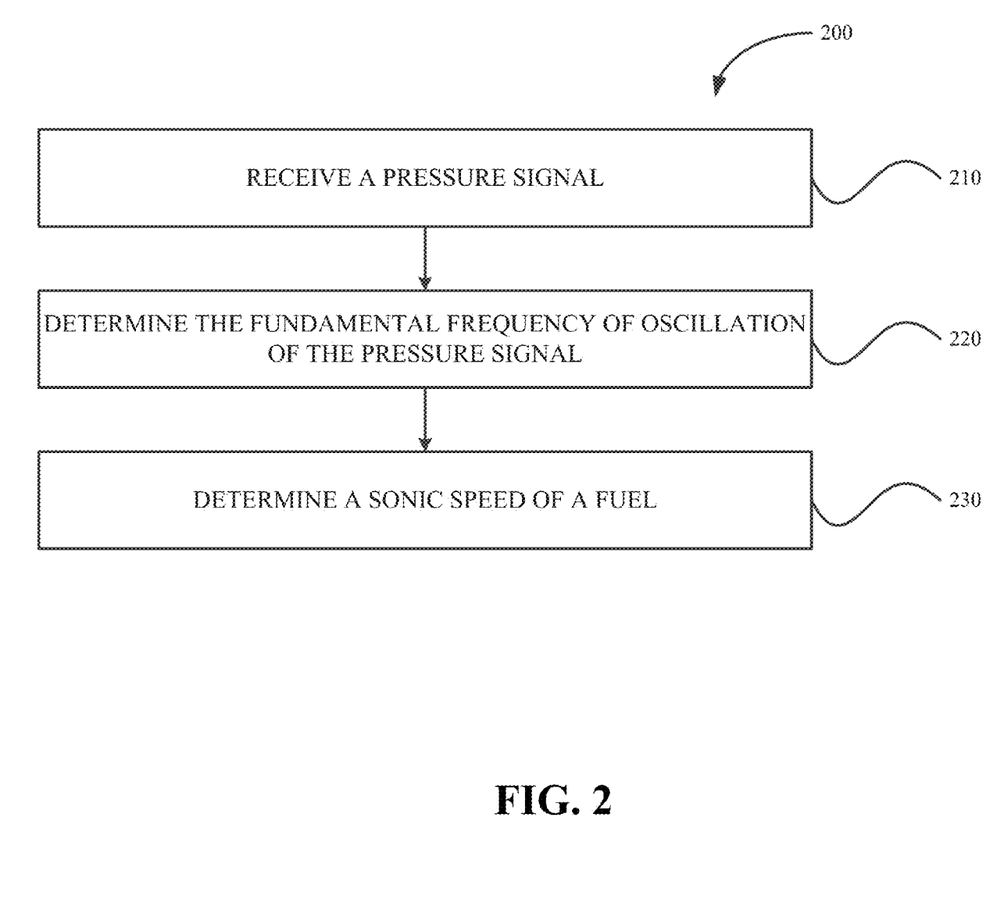
FIG. 2 illustrates a diagnostic method for determining a sonic speed according to various embodiments.

FIG. 2 illustrates diagnostic method 200 according to various embodiments. Diagnostic method 200 may include receiving, by a pressure interpreter (i.e., a pressure sensor), a pressure signal (step 210), determining, by a determiner in communication with the pressure interpreter, a fundamental frequency of oscillation of the pressure signal (step 220), and determining, by the determiner, a sonic speed of a fuel based on the fundamental frequency of oscillation (step 230).

As used herein and similar to various system claims, the interpreter and determiner in the various methods are not particularly limited. In various embodiments, the interpreter and determiner may be separate components (e.g., of a diesel engine) and in other embodiments may be the same component.

Figure 3:
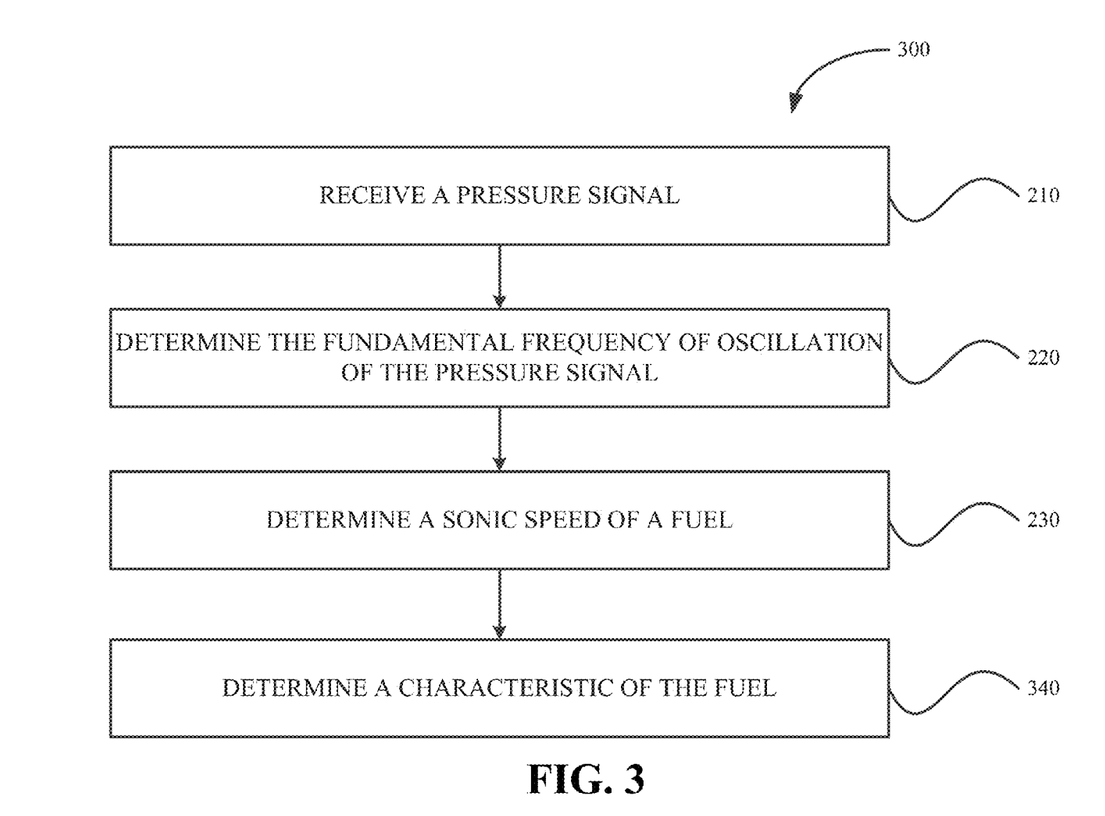
FIG. 3 illustrates a diagnostic method for determining a characteristic of a fuel according to various embodiments.

FIG. 3 illustrates diagnostic method 300 for determining a characteristic of the fuel (step 340). As used herein, the term "characteristic" may include at least one of a temperature of the fuel, a classification of the fuel, or a composition of the fuel, or combinations thereof. From this classification or composition of the fuel from the determiner, many useful characteristics such as the heating value or density of the fuel can be estimated. Similar to diagnostic method 200, diagnostic method 300 also may include receiving, by a pressure interpreter, a pressure signal (step 210), determining, by a determiner in communication with the pressure interpreter, a fundamental frequency of oscillation of the pressure signal (step 220), and determining, by the determiner, a sonic speed of a fuel based on the fundamental frequency of oscillation (step 230).

Figure 4:
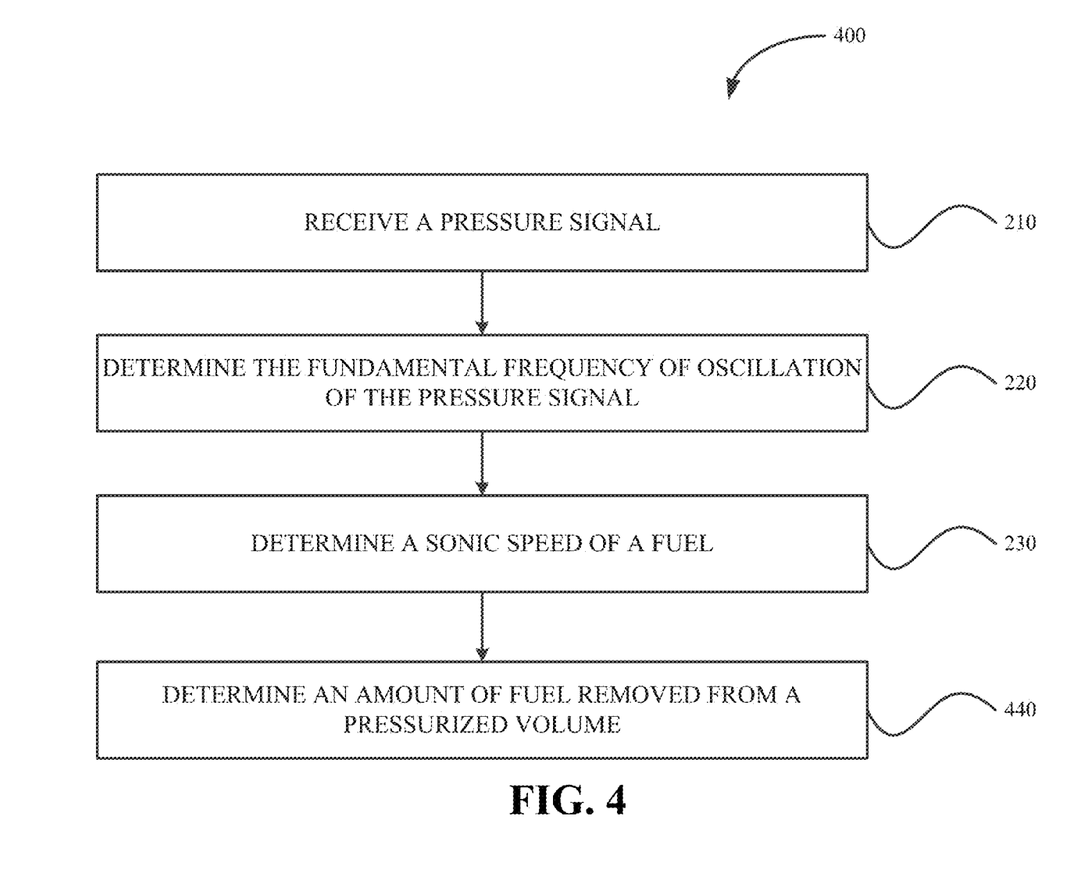
FIG. 4 illustrates a diagnostic method for determining an amount of fuel removed from a pressurized volume according to various embodiments.

FIG. 4 illustrates diagnostic method 400 for determining an amount of fuel removed from a pressurized volume. Similar to diagnostic methods 200 and 300, diagnostic method 400 may include receiving, by a pressure interpreter, a pressure signal (step 210), determining, by a determiner in communication with the pressure interpreter, a fundamental frequency of oscillation of the pressure signal (step 220), and determining, by the determiner, a sonic speed of a fuel based on the fundamental frequency of oscillation (step 230). Furthermore, diagnostic method 400 may also include determining an amount of fuel removed from a pressurized volume with the sonic speed (step 440). The pressurized volume is not particularly limited and may include pressurized volumes that are fixed, for example, a rail in an engine.

Figure 5:
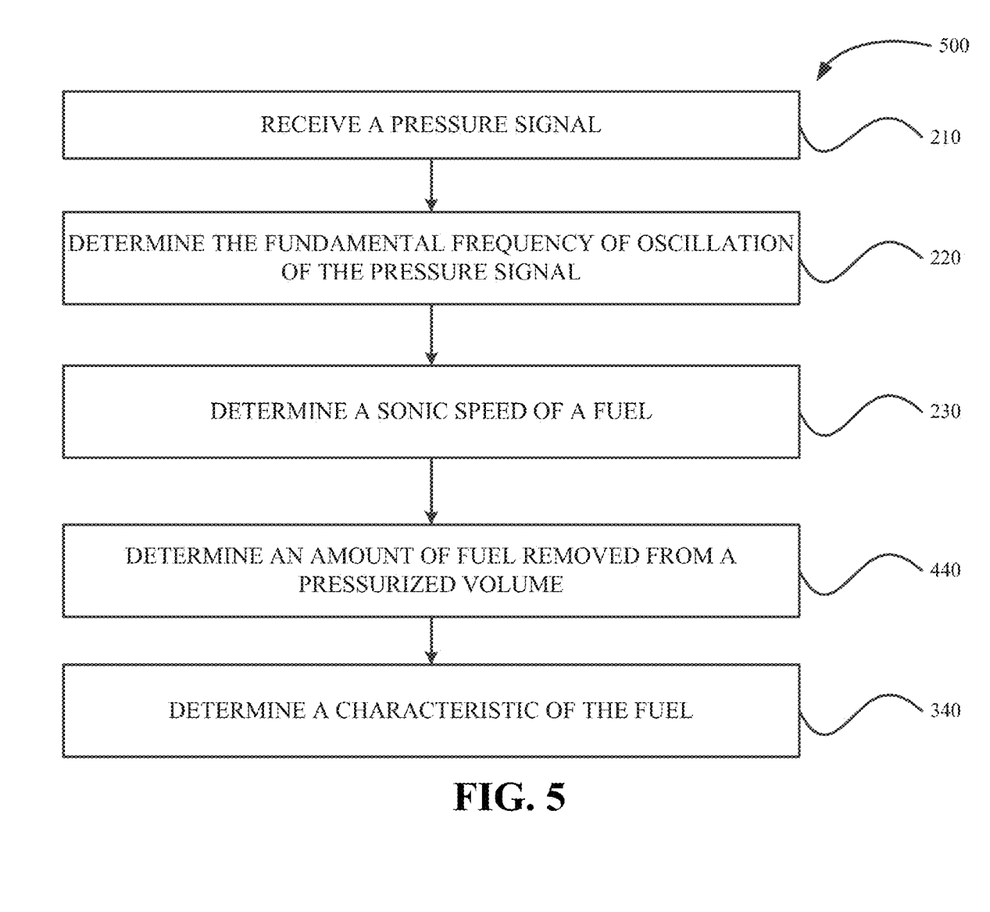
FIG. 5 illustrates a diagnostic method according to various embodiments.

In various embodiments, diagnostic method 300 and diagnostic 400 may be combined, for example, as illustrated in FIG. 5. FIG. 5 illustrates a diagnostic method that includes determining an amount of fuel removed from a pressurized volume with the sonic speed (step 440) and determining a characteristic of the fuel (step 340).

The methods disclosed herein are not particularly limited and may occur continuously, once during operation of an engine, or may occur based on predetermined parameters. As used herein, the term "predetermined parameters" may include predetermined time intervals, levels of engine performance (e.g., revolutions per minute (RMP), fuel input received), or after an event, such as refueling.

Figure 6:
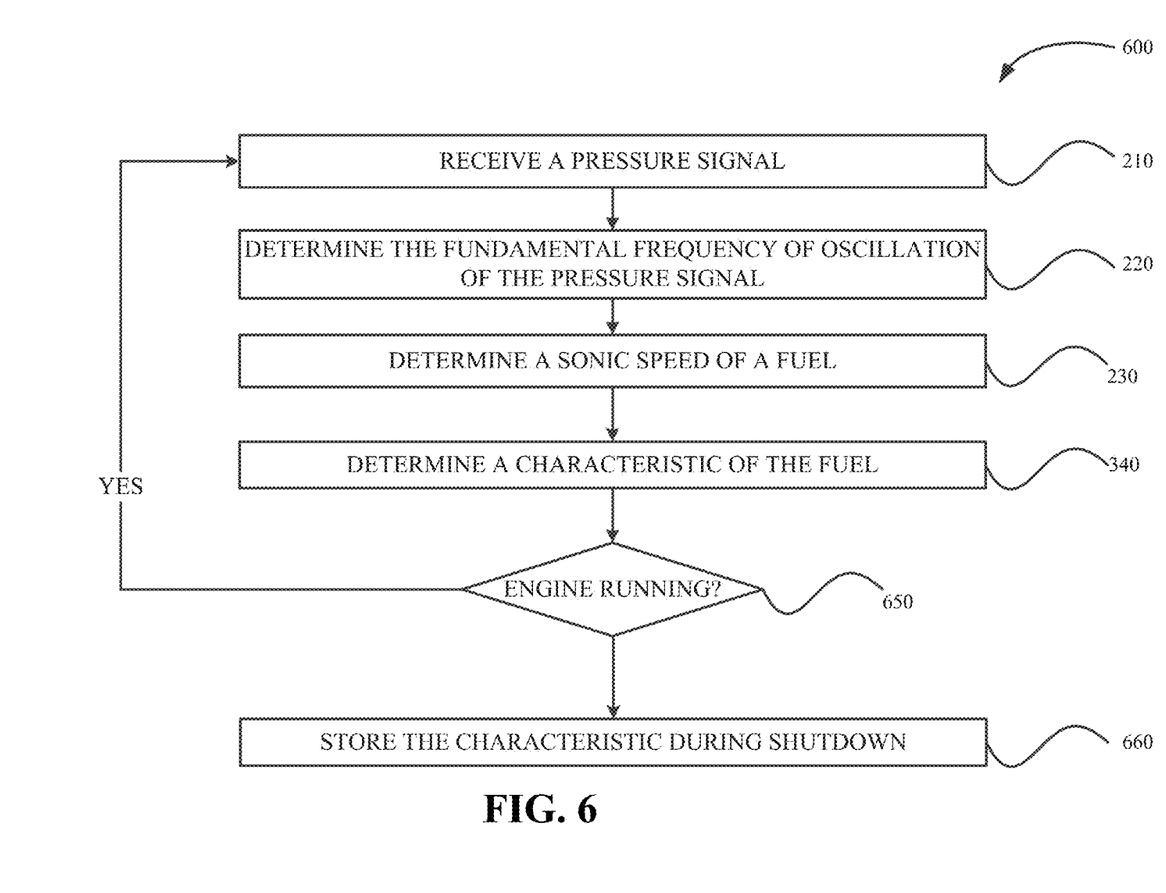
FIG. 6 illustrates a continuous diagnostic method according to various embodiments.

FIG. 6 illustrates an exemplary continuous diagnostic method 600 according to various embodiments. The term "continuous" as used herein may include methods that repeat continuously during operation of an engine. Method 600 may comprise receiving, by a pressure interpreter, a pressure signal (step 210), determining, by a determiner in communication with the pressure interpreter, a fundamental frequency of oscillation of the pressure signal (step 220), and determining, by the determiner, a sonic speed of a fuel based on the fundamental frequency of oscillation (step 230). Continuous diagnostic method 600 may also include the determination whether the engine is running (step 650). If the engine is running, then step 210, 220, 230, and 340 may be repeated. If the engine is no longer running, then the characteristic of the fuel may be stored during shutdown of an engine (step 660). Thus, in various embodiments, the characteristic may store by the determiner during operation of the engine, during shut-down, during start-up, or combinations thereof.

Various benefits include the ability to compensate for engine installation differences that affect the ambient conditions of the fuel system, thereby producing a unique fuel temperature dependency on the measureable temperature inputs.

Additional benefits, such as embodiments that use on-line regression, may include the avoidance of a costly calibration exercise to fit the temperature model. With on-line regression, the calibration of sonic speed becomes partially automated and, thus, the accuracy and precision of the various methods and models may become dependent merely on operation of the engine in a sufficient number of operating and environmental conditions to establish each coefficient with reasonable confidence.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." For example, the use of the term "frequency" is not intended to mean only one and only one frequency. Thus, in various embodiments and/or configurations, multiple fundamental oscillation frequencies from which reinforcing or unique information about the system and/or fuel may be obtained.

Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

Systems, methods and apparatus are provided herein. In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic with the benefit of this disclosure in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A diagnostic system comprising:
a pressure sensor;
a determiner in communication with the pressure sensor, wherein the determiner is structured to estimate a sonic speed of a fuel in response to identification of a fundamental oscillation frequency, a temperature of the fuel and a pressure of the fuel.

2. The diagnostic system of claim 1, wherein the determiner receives a rail pressure signal from the pressure sensor.

3. The diagnostic system of claim 1, wherein the determiner determines a mass of fuel removed from a pressurized volume.

4. The diagnostic system of claim 3, wherein the pressurized volume is a fixed volume.

5. The diagnostic system of claim 1, wherein the determiner determines a characteristic of the fuel.

6. The diagnostic system of claim 5, wherein the characteristic includes at least one of the temperature of the fuel, a classification of the fuel, a composition of the fuel, and combinations thereof.

7. The diagnostic system of claim 6, wherein the determiner determines a mass of fuel removed from a pressurized volume.

8. The diagnostic system of claim 5, wherein the characteristic is stored by the determiner during at least one of operation of the engine, shut-down, start-up, and combinations thereof.

9. An engine comprising:
a pressure sensor;
a determiner in communication with the pressure sensor, wherein the determiner is structured to estimate a sonic speed of a fuel in response to identification of a fundamental oscillation frequency, a temperature of the fuel and a pressure of the fuel.

10. The engine of claim 9, wherein the engine is a diesel engine.

11. The engine of claim 9, wherein the engine is a flex fuel engine.

12. A diagnostic method comprising:
receiving, by a pressure interpreter, a pressure signal;
determining, by a determiner in communication with the pressure interpreter, a fundamental frequency of oscillation of the pressure signal; and
determining, by the determiner, a sonic speed of a fuel in response to determining the fundamental frequency of oscillation, a temperature of the fuel and a pressure of the fuel.

13. The diagnostic method of claim 12, further comprising determining an amount of fuel removed from a pressurized volume with the sonic speed.

14. The diagnostic method of claim 12, further comprising determining a characteristic of the fuel with the sonic speed.

15. The diagnostic method of claim 14, wherein the characteristic of the fuel includes at least one of the temperature of the fuel, a classification of the fuel, an octane rating of the fuel, a composition of the fuel, and combinations thereof.

16. The diagnostic method of claim 12, wherein the method repeats continuously during operation of an engine.

17. The diagnostic method of claim 16, wherein the engine is a diesel engine.

18. The diagnostic method of claim 14, wherein the determiner stores the characteristic during shutdown of an engine.

19. The diagnostic method of claim 12, wherein the pressure interpreter is the determiner.

20. The diagnostic method of claim 12, wherein the method repeats in response to a predetermined parameter.

* * * * *